United States Patent [19]

Otton

[11] 4,233,230
[45] Nov. 11, 1980

[54] PROCESS FOR PREPARING OLEFINS BY METATHESIS OF CYCLIC OLEFINS WITH ACYCLIC OLEFINS

[75] Inventor: Jean Otton, Ecully, France

[73] Assignee: Rhone-Poulenc Industries, Paris, France

[21] Appl. No.: 902,709

[22] Filed: May 4, 1978

[30] Foreign Application Priority Data

May 6, 1977 [FR] France .................................. 77 13804
Apr. 24, 1978 [FR] France .................................. 78 11986

[51] Int. Cl.³ ............................................ C07C 67/343
[52] U.S. Cl. ................................ 260/410.9 R; 260/405;
260/408; 260/410.5; 260/410.6; 260/410.9 N;
560/105; 560/111; 560/112; 560/113; 560/146;
560/190; 560/193; 560/241; 560/246; 568/857;
568/858; 568/877; 585/600; 585/603; 585/608;
570/237
[58] Field of Search ................ 560/241, 246, 190, 193,
560/146, 105, 111, 112, 113; 260/410.9 A, 410.9
M, 654 R, 408, 405, 410.5, 410.6

[56] References Cited

U.S. PATENT DOCUMENTS 3,974,196   8/1976   Nakamura et al. ................ 260/410.9

OTHER PUBLICATIONS

Ichikawa et al. I, Yakagaku, 1976 25(11) 779-783, as cited in Chem. Abstracts, 86, 88856t (1977).
Ichikawa et al. II, J. of Catalysis, 44, 416-420 (1976).
Verkuijlen et al., Fette, Seifen, Anstrechm, 1976, 78(11) 444-447 (1976).
Van Dam et al. (I), J.C.S. Chem. Comm., 1972 (22), 1221 (1972).
Wilson et al., J. Org. Chem. 41(24) pp. 3928-3929 (1976).
Van Dam et al. (II), J. Am. Oil Chem. Soc., 1974, 51(9), 389-392 (1974).
Verkuijlen et al., J.C.S. Chem. Comm, 1974 (19), 793-794, (1974).
Takagi et al., as cited in Chem. Abstracts 83, 130804g (1975).

*Primary Examiner*—Jane S. Myers
*Attorney, Agent, or Firm*—Burns, Doane, Swecker & Mathis

[57] ABSTRACT

A process for preparing esters and halides is disclosed comprising the step of reacting a cyclic olefin having the formula I

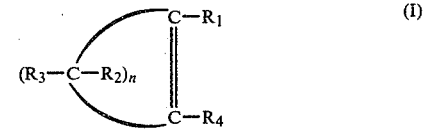

wherein
$R_1$ and $R_4$ are the same or different from each other and each represents hydrogen, methyl, or ethyl;
$R_2$ and $R_3$ are the same or different from each other and each represents hydrogen or alkyl containing 1 to 5 carbon atoms; and
n represents a whole number from 2 to 12, with an acyclic olefin having the formula II

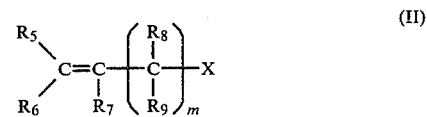

wherein
$R_5$ represents hydrogen, methyl, ethyl or the group

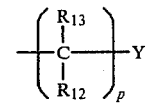

wherein $R_{12}$ and $R_{13}$ are the same or different from each other and each represents hydrogen or alkyl containing 1 to 5 carbon atoms;
Y represents halogen; an acyloxy group $R_{14}$—CO—O wherein $R_{14}$ represents alkyl containing 1-12 carbon atoms, phenyl or phenyl alkyl containing 7-12 carbon atoms, or an oxycarbonyl group $R_{15}$—O—CO wherein $R_{15}$ represents alkyl containing 1-12 carbon atoms, phenyl or phenyl alkyl containing 7-12 carbon atoms;
p represents a whole number from 1-12 except when Y is an $R_{14}$CO—O group wherein p is from 2 to 12.
$R_6$ and $R_7$ are the same or different from each other and each represents hydrogen, methyl, or ethyl;
$R_8$ and $R_9$ are the same or different from each other and each represents hydrogen or alkyl containing 1 to 5 carbon atoms;
X represents halogen; an acyloxy group $R_{10}$—CO—O—, wherein $R_{10}$ represents alkyl containing 1-12 carbon atoms, phenyl, or phenylalkyl containing 7-12 carbon atoms, or an oxycarbonyl group $R_{11}$—O—CO, wherein $R_{11}$ represents alkyl containing 1-12 carbon atoms, phenyl, or phenylalkyl containing 7-12 carbon atoms,
m represents a whole number from 1-12 except when X is an $R_{10}$—CO—O— group wherein m is from 2 to 12 in the presence of a catalytic composition comprising a halogen-tungsten salt and a reducing agent which is an organic tin compound.

22 Claims, No Drawings

PROCESS FOR PREPARING OLEFINS BY METATHESIS OF CYCLIC OLEFINS WITH ACYCLIC OLEFINS

BACKGROUND OF THE INVENTION

This process permits the preparation of unsaturated esters and halides containing straight chained hydrocarbon groups of a predetermined chain length which are valuable intermediates from which the corresponding straight chained alcohols, diols and diesters can be obtained by means of hydrogenation or saponification.

1. Field of the Invention

The present application relates to a process for preparing olefins by metathesis of two different olefins. The term metathesis, as used in the present specification, is meant to connote the interaction of two structurally different olefins. In particular, the present invention pertains to a process for preparing olefins by metathesis of at least two different olefins, only one of which comprises at least one functional group.

2. Description of the Prior Art

Several examples of this type of reaction are known in the prior art literature. For example, in an article of P. B. Van Dam, M.C. Mittelmeyer, and C. Boelhouwer in J.C.S. Chem. Comm. 1972, 1221, a metathesis between methyl oleate and hexene-3 in the presence of a catalyst, containing tungsten hexachloride and tetramethyl-tin, is disclosed. The French Pat. No. 2,252,314 also pertains to the metathesis of an olefin and an olefin comprising a functional group in the presence of a catalyst, which is a combination of a component selected from the group of tungsten compounds, molybdenum compounds, and rhenium compounds and an organic aluminum compound, containing at least one carbon-aluminum-bond.

One of the major objects of the metathesis-reaction according to the present invention resides in the preparation of straight-chained unsaturated esters or diesters which are valuable intermediates, which can be transformed into the corresponding straight-chained saturated alcohols or diols by means of complete hydrogenation or saponification or into the corresponding saturated monoesters or diesters by means of moderate hydrogenation. Such alcohols, containing between about 12 and 18 carbon atoms, are known to possess excellent detergent activities and to be totally biologically decomposable. The saturated diesters are used as comonomers in polycondensation reactions with, for example, diamines or diols. These straight-chained, unsaturated esters can be obtained directly by metathesis of two different olefins, one of which comprises at least one appropriate ester group, or indirectly by methathesis of two different olefins, one of which comprises at least one group which subsequently can readily be replaced by an ester group.

In the preparation of acyclic olefins comprising at least one functional group, it is important that the chain-length of the straight-chained portions of the resulting molecules can be adjusted to a desired value, according to the intended use of the products. Thus, in the before-mentioned particular case of preparing products which are adapted for detergent purposes, it is important that the products comprise hydrocarbon groups of a sufficient chain-length, that is a chain-length equivalent to from about 12 to about 18 carbon atoms. Moreover in the case of products to be used in polycondensation reactions, it is important that the products have a well defined chain length to ensure stable thermomechanical and mechanical properties to the polymers. It is difficult to obtain a desired chain-length, if an olefin comprising a functional group and a straight-chained olefin are used as starting materials. Such olefins, which must contain a relatively high number of carbon atoms, are not readily available in amounts necessary for industrial production. On the other hand, straight-chained olefins may undergo isomerization at the double bound during the metathesis and this would reduce the selectivity of the reaction in forming compounds containing straight-chained hydrocarbon groups.

SUMMARY OF THE INVENTION

It is an object of the present invention to provide a process for preparing olefins containing at least one functional group and having a predetermined chain-length, wherein the abovementioned difficulties are avoided.

It is a further object of the present invention to provide a process, whereby unsaturated diesters with a well defined chain length can be readily prepared on an industrial scale.

It is a further object of the present invention to provide a process, whereby unsaturated esters containing hydrocarbon groups having a straight-chain length of from about 12 to about 18 carbon atoms can be readily prepared on an industrial scale.

It is further object of the present invention to provide a process for reacting an olefin containing at least one functional group with a second olefin, wherein a high selectivity of the reaction with regard to the formation of acyclic olefins containing the functional group and straight-chained hydrocarbon groups, is achieved.

In order to accomplish the foregoing objects according to the present invention, there is provided a process for preparing olefins which comprises the step of reacting a cyclic olefin having the formula I

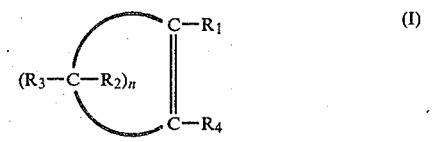

wherein $R_1$ and $R_4$ are the same or different from each other and each represents hydrogen methyl or ethyl $R_2$ and $R_3$ are the same or different from each other and each represents hydrogen or alkyl containing 1 to 5 carbon atoms, p1 n represents a whole number from 2 to 12, with an acyclic olefin having the formula II

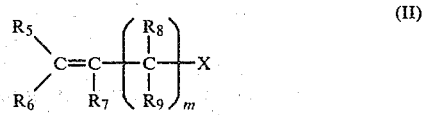

wherein $R_5$ represents hydrogen, methyl, ethyl or the group

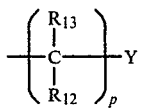

wherein $R_{12}$ and $R_{13}$ are the same or different from each other and each represents hydrogen or alkyl containing 1 to 5 carbon atoms;

Y represents halogen; an acyloxy group $R_{14}$—CO—O—wherein $R_{14}$ represents alkyl containing 1–12 carbon atoms, phenyl or phenyl alkyl containing 7–12 carbon atoms; or an oxycarbonyl group $R_{15}$—O—CO— wherein $R_{15}$ represents alkyl containing 1–12 carbon atoms, phenyl or phenylalkyl containing 7–12 carbon atoms p represents a whole number from 1–12 except when Y is an $R_{14}$CO—O group wherein p is from 2 to 12

$R_6$ and $R_7$ are the same or different from each other and each represents hydrogen, methyl or ethyl, $R_8$ and $R_9$ are the same or different from each other and each represents hydrogen or alkyl containing 1 to 5 carbon atoms, x represents halogen, an acyloxy group $R_{10}$—CO—O—, wherein $R_{10}$ represents alkyl containing 1–12 carbon atoms, phenyl or phenylalkyl, containing 7–12 carbon atoms or an oxycarbonyl group $R_{11}$—O—CO—, wherein $R_{11}$ represents alkyl containing 1–12 carbon atoms, phenyl or phenylalkyl, containing 7–12 carbon atoms, m represents a whole number from 1–12 except when X is an $R_{10}$—CO—O group wherein m is from 2 to 12 in the presence of a catalytic composition comprising a halogen-tungsten salt and a reducing agent which is an organic tin compound.

The process according to the present invention leads to unsaturated esters and halides and is especially suitable for the preparation of unsaturated esters containing straight chained hydrocarbon groups of a predetermined chain length, e.g., unsaturated esters containing hydrocarbon groups having a chain length of from about 10–18 carbon atoms, which are valuable intermediates for the preparation of straight chained alcohols which are useful as detergent agents or for the preparation of straight chained diesters which are useful as monomers for polycondensation reactions.

There is further provided according to the present invention a process for preparing alcohols or diols which comprises the step of hydrogenating the unsaturated esters or diesters which are obtained by the above described process into the corresponding alcohols.

Further objects, features, and advantages of the present invention will become apparent from the detailed description of the invention and its preferred embodiments which follows.

DETAILED DESCRIPTION OF THE INVENTION AND THE PREFERRED EMBODIMENTS THEREOF

It has been found that according to the present invention unsaturated compounds containing at least one functional group and hydrocarbon groups of a predetermined chain-length, in particular unsaturated esters, or diesters can be readily obtained in the process according to the present invention, which is suitable for industrial production of these unsaturated compounds. The before-mentioned difficulties, which are related to the production of unsaturated compounds containing a functional group and hydrocarbon groups of a predetermined chain-length are avoided according to the present invention, by using an acyclic olefin containing at least one functional group, and a cyclic olefin as starting materials for the metathesis reaction. If this reaction is carried out in the presence of the above defined catalyst, the use of a cyclic olefin permits to obtain the formation of hydrocarbon groups containing the desired number of carbon atoms during the reaction with the acyclic olefin comprising at least one functional group under process conditions which are easy to provide and are satisfactory for industrial production. The halogen-tungsten salt within the catalyst composition, preferably is a tungsten salt wherein all or part of the oxygen atoms of a tungsten oxide are replaced by halogen, that is a neutral or a basic tungsten halide, or a tungsten oxide-halide. The halide preferably is chloride, bromide, or fluoride. Examples of such suitable halogen-tungsten salts, are the following:

$WCl_6$, $WOCl_4$, $WBr_6$, $WOBr_4$, and $WF_6$.

Among the foregoing salts $WCl_6$ is preferred.

The term "reducing organic tin compound" as used in the present specification and claims is defined to mean an organic tin compound which is capable of reducing the tungsten salt. The reducing organic tin compound of the catalyst composition suitably is a compound of the formula $Sn(R)_4$, wherein R is alkyl, in particular lower alkyl. Among these tetraalkyltin compounds $Sn(CH_3)_4$ is preferrred.

According to a preferred embodiment of the invention, a catalyst composition is used which is essentially consisting of $WCl_6$ and $Sn(CH_3)_4$.

Among the cyclic olefins of formula I olefins wherein $R_1$, $R_2$, $R_3$, and $R_4$ represent hydrogen or methyl are preferred. For example, the following cyclic olefins are particularly suitable:

cyclobutene, cyclopentene, cycloheptene, cyclooctene, cyclodecene, cyclododecene, 4-methylcyclooctene, 4,5dimethylcyclooctene, 3-methylcyclopentene, 1,8-dimethylcyclooctene, 1,4,5,8-tetramethylcyclooctene.

The process according to the present invention is especially suited for preparing unsaturated ester containing straight-chained hydrocarbon groups of a predetermined chain length. For this purpose unsubstituted cycloolefins are preferred, in particular cyclopentene, cyclooctene, cyclodecene, and cyclododecene.

In acyclic olefins of formula II, m and p preferably are a number between 1 and 6. In the case of formula II, the substituents $R_{10}$, $R_{11}$, $R_{14}$ or $R_{15}$ preferably are lower alkyl. The substituents $R_5$, $R_6$, $R_7$, $R_8$, $R_9$, $R_{12}$ and $R_{13}$ preferably are hydrogen or methyl, whereby hydrogen is most preferred in the case of the preparation of unsaturated esters containing straight-chained hydrocarbon groups of a predetermined chain length.

The following acyclic monofunctional olefins of formula II are particularly suitable:

methylbutene-3-oate, ethylbutene-3-oate, methylpentene-4-oate, ethylpentene-4-oate, methylpentene-3-oate, ethylpentene-3-oate, methylhexene-5-oate, ethylhexene-5-oate, 4-acetoxybutene-1, 5-acetoxypentene-1, 6-acetoxyhexene-1, 4-benzoyloxybutene-1, benzylbutene-3-oate, benzylpentene-3-oate, methyl-3,3-dimethylpentene-4-oate, 4-chlorobutene-1, 5-chloropentene-1, 6-chlorohexene-1, 4-bromobutene,-1, 6-bromohexene-1.

Among the foregoing acyclic monofunctional olefins of formula II, the following are especially preferred:

methylbutene-3-oate, ethylbutene-3-oate, methylpentene-3-oate, ethylpentene-4-oate, 4-acetoxybutene-1, 6-acetoxyhexene-1.

The following acyclic bifunctional olefins of formula (II) are particularly suitable:

methyl or ethyl-hexen-3-dioate-1,6; methyl or ethyl-octen-4-dioate-1,8; methyl or ethyl-octene-3-dioate-1,8; methyl or ethyl-decen-5-dioate-1,10; 1,6-diacetoxy-3-hexene; 1,8-diacetoxy-3 or 4 octene; 1,10-diacetoxy-3 or 4 or 5 decene.

Among the foregoing acyclic bifunctional olefins of formula (II) the following are especially preferred:

methyl or ethyl hexen-3-dioate-1,6 and 1,6-diacetoxy-3-hexene.

The reaction of a cyclic olefin of formula I with an acyclic olefin of formula II according to the present invention leads to the formation of compounds of the following formula III.

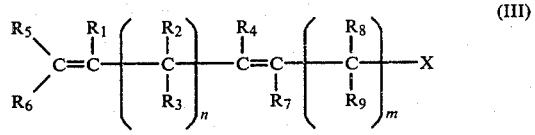

wherein $R_1$, $R_2$, $R_3$, $R_4$, $R_5$, $R_6$, $R_7$, $R_8$, $R_9$, n, m and X are as define above. The process according to the present invention is especially suited for the preparation of such compounds of formula III, in particular monoesters of formula III, preferably esters and diesters. The following are examples of monofunctional compounds of formula III which can be prepared by the process according to the present invention:

12-acetoxydodecadiene-1,9; 12-propionyloxydodecadiene-1,9; 13-acetoxytridecadiene-1,9; 13-propionyloxydodecadiene-1,9; 14-acetoxytetradecadiene-1,9; 14-propionyloxytetradecadiene-1,9; ethyldodecadiene-3,11-1-oate; methyldodecadiene-3,11-1-oate; methyltridecadiene-4,12-1-oate; ethyltridecadiene-4,12-1-oate; methyltetradecadiene-5,13-1-oate; ethyltetradecadiene-5,13-1-oate; 14-acetoxytetradecadiene-1,11; 15-acetoxypentadecadiene-1,11; 16-acetoxyhexadecadiene-1,11; 14-propionyloxytetradecadiene-1,11; 15-propionyloxypentadecadiene-1,11; 16-propionyloxyhexadecadiene-1,11; 15-butyryloxytetradecadiene-1,11; 15-butyryoxypentadecadiene-1,11; 16-butyryloxyhexadecadiene-1,11; 14-valeryloxytetradecadiene-1,11; 15-valeryloxypentadecadiene-1,11; 16-valeryloxyhexadecadiene-1,11; methyltetradecadiene-3,13-1-oate; ethyltetradecadiene-3,13-1-oate; methylpentadecadiene-4,14-1-oate; ethylpentadecadiene-4,14-1-oate; methylhexadecadiene-5,15-1-oate; ethylhexadecadiene-5,15-1-oate.

The esters of formula III can be transformed into alcohols by means of hydrogenation or saponification. The hydrogenation can be carried out in a conventional manner.

The following alcohols are obtained by hydrogenating or saponificating the above listed unsaturated esters:
dodecanol,
tridecanol
tetradecanol
pentadecanol,
hexadecanol.

The following are examples of bifunctional compounds which can be prepared by the process by the process according to the present invention:
Methyl or ethyl tetradecadien-3,11-dioate-1,14;
Methyl or ethyl hexadecadien-4,12-dioate-1,16;
Methyl or ethyl hexadecadien-3,11-dioate-1,16;
Methyl or ethyl octadecadien-3,11-dioate-1,18;
Methyl or ethyl octadecadien-4,12-dioate-1,18;
Methyl or ethyl octadecadien-5,13-dioate-1,18;
1,14-diacetoxy-3,11-tetradecadiene;
1,16-diacetoxy-4,12-hexadecadiene;
1,16-diacetoxy-3,11-hexadecadiene;
1,18-diacetoxy-5,13-octadecadiene;
1,18-diacetoxy-4,12-octadecadiene;
1,18-diacetoxy-3,11-octadecadiene.

The following diols are obtained by complete hydrogenation or saponification of the above listed unsaturated diesters:
1,14-tetradecanediol
1,16-hexadecanediol
1,18-octadecanediol.

The following saturated diesters are obtained by moderate hydrogenation of the above listed unsaturated diesters:
Methyl or ethyl-1,14 tetradecanedioate
Methyl or ethyl-1,16 hexadecanedioate
Methyl or ethyl-1,18 octadecandioate
1,14 diacetoxytetradecane,
1,16 diacetoxyhexadecane,
1,18 diacetoxyoctadecane.

The reaction is suitably carried out in the presence of a solvent. Preferably halogenated aromatic solvents, in particular halogenated benzene derivatives, are used as a solvent. Among these, chlorobenzene is especially preferred. Other equivalent aromatic solvents may also be used. Such equivalent solvents are aromatic solvents, which comprise at least one substituent which, like halogen substituents desactivates the aromatic nucleus, yet does not interfere with the action of the catalyst; that is solvents, which permit the catalyst to interact simultaneously with the cyclic olefin and the olefin containing the functional group.

Accordinng to a preferred embodiment of the invention the reaction is carried out by introducing the various reactants, into the reaction zone in three steps; in a first step, the cyclic olefin of formula I and the acyclic olefin of formula II containing the functional group are introduced into the reactor, whereby the sequence for introducing these two components is not essential; in a second step, the halogenated tungsten salt is introduced, preferably in form of a solution or suspension in the solvent; and in a third step, after obtaining a homogeneous solution, the reducing organic tin compound is added.

The solvent may also be added in the first step and then the halogenated tungsten salt be added later in solid form.

The homogenization of the solution goes together with a complex-formation between the reactants and the halogenated tungsten salt which in complexed form is soluble in the reaction medium. The reducing organic tin compound serves to bring the tungsten into the appropriate state of oxidation.

Suitably, the reaction is carried out at a temperature between about −20° and about 300° C. Preferably, the reaction temperature is between about 50° and about 150° C.

The reaction pressure is not critical; suitably the reaction takes place under atmospheric pressure.

With regard to the combination of the halogenated tungsten salt and the reducing organic tin compound, which are used in catalytically effective amounts, it has been found that in the process according to the present invention, the best results are obtained, if in the catalyst combination the molar ratio between the reducing organic tin compound and the halogen-tungsten salt is from about 0.5 to about 4, and preferably is from about 1 to about 2.

Preferably such amounts of cyclic olefin and acyclic olefin are used that the molar ratio between the cyclic olefin and the acyclic olefin containing the functional group is from about 0.5 to about 2.

The olefin starting materials, the catalyst materials, and the solvents should be completely dehydrated and degassed, and the reaction should be carried out under inert atmosphere (e.g., nitrogen or argon).

The following examples are intended to further illustrate the invention without limiting it.

EXAMPLE I: Reaction between cyclooctene and 4-acetoxybutene-1 of the formula $$CH_2=CH-(CH_2)_2-O-CO-CH_3$$

1.15 g (10.1 mM) of 4-acetoxybutene-1, 2.4 ml (18.4 mM) of cyclooctene and 24 ml of a solution which was obtained by mixing 761 mg of $WCl_6$ in 47 ml of chlorobenzene (this amount corresponded to 0.96 mM of $WCl_6$) were successively introduced into a small, round-bottomed 50 ml glass flask, which was equipped with an inlet for dried nitrogen and an opening which was closed by a self-closing type of stopper, and which was previously freed from its air- and moisture content by heating under vaccuum and subsequent cooling under dry nitrogen.

The reaction mixture, which was blue in the beginning, changed to a dark red color then to light red and translucent (homogenous medium). The mixture was heated to a temperature of about 50° C. under atmospheric pressure. Then 0.13 ml (0.96 mM) of $Sn(CH_3)_4$ were added. The color of the reaction medium changed to red, which was becoming darker and darker, then to red-black, and a gas development was observed (the gas undoubtedly was ethylene which was formed by disproportionation of 4-acetoxybutene-1 with itself). The progress of the reaction was observed by gas chromatography of samples, which were periodically taken from the reaction mixture. In order to stop any further continuation of the reaction in the samples, a small amount of alcohol was added thereto.

After a reaction period of one hour at 50° C., the degree of transformation of the cyclooctene was 50% and that of 4-acetoxybutene-1 was 60%. The selectivity with regard to the formation of 12-acetoxydodecadiene-1,9 was about 45%. The analysis of the reaction mixture by means of combined gas chromatography and mass spectrography showed the presence of the following expected components in the reaction product:

$CH_2=CH-(CH_2)_6-CH=CH_2$ (decadiene-1,9), $CH_2=CH-(CH_2)_6-CH=CH-(CH_2)_6-CH=CH_2$, $$CH_3-\underset{\underset{O}{\|}}{C}-O-(CH_2)_2-CH=CH-(CH_2)_2-O-\underset{\underset{O}{\|}}{C}-CH_3,$$

$CH_2=CH-(CH_2)_6-CH=CH-(CH_2)_2-O-\underset{\underset{O}{\|}}{C}-CH_3$ (12-acetoxydodecadiene-1,9), $$CH_3-\underset{\underset{O}{\|}}{C}-O-(CH_2)_2-CH=CH-(CH_2)_6-CH=CH-(CH_2)_2-O-\underset{\underset{O}{\|}}{C}-CH_3,$$

$$CH_2=CH-(CH_2)_6-CH=CH-(CH_2)_6-CH=CH-(CH_2)_2-O-\underset{\underset{O}{\|}}{C}-CH_3.$$

EXAMPLE II: Reaction between cyclooctene and 5-acetoxypentene-1 having the formula $$CH_2=CH-(CH_2)_3-O-\underset{\underset{O}{\|}}{C}-CH_3.$$

The same procedure as is described in Example I was used. The amount of cyclooctene was 18.4 mM. The amount of 5-acetoxypentene-1 was 9.95 mM. The amount of $WCl_6$ was 0.96 mM and the amount of $Sn(CH_3)_4$ was 0.96 mM.

After a reaction period of three hours at 50° C., the degree of transformation of the cyclooctene was 81.6% and that of 5-acetoxypentene-1 was 60%.

The selectivity with regard to the formation of 13-acetoxytridecadiene-1,9 was about 30%.

The analysis of the reaction mixture by means of combined gas chromatography and mass spectrography showed the presence of the following expected components in the reaction product:

$CH_2=CH-(CH_2)_6-CH=CH_2$ (decadiene-1,9), $CH_2=CH-(CH_2)_6-CH=CH-(CH_2)_3-O-\underset{\underset{O}{\|}}{C}-CH_3$ (13-acetoxytridecadiene-1,9), $CH_2=CH-(CH_2)_6-CH=CH-(CH_2)_6-CH=CH_2$, $$CH_3=\underset{\underset{O}{\|}}{C}-O-(CH_2)_3-CH=CH-(CH_2)_6-CH=CH-(CH_2)_3-O-\underset{\underset{O}{\|}}{C}-CH_3,$$

$$CH_3=\underset{\underset{O}{\|}}{C}-O-(CH_2)_3-CH=CH-(CH_2)_3-O-\underset{\underset{O}{\|}}{C}-CH_3,$$

-continued $$CH_2=CH-(CH_2)_6-CH=CH-(CH_2)_6-CH=CH-(CH_2)_3-O-\underset{\underset{O}{\|}}{C}-CH_3.$$

EXAMPLE III: Reaction between cyclooctene and 6-acetoxyhexene-1 having the formula $$CH_2=CH-(CH_2)_4-O-\underset{\underset{O}{\|}}{C}-CH_3.$$

The same procedure as described in Example I was used. The amount of cyclooctene was 18.9 mM. The amount of 6-acetoxyhexene-1 was 12.9 mM. The amount of $WCl_6$ was 0.96 mM, and the amount of $Sn(CH_3)_4$ was 0.96 mM.

After a reaction period of one hour at 50° C., the degree of transformation of the cyclooctene was 33% and that of 6-acetoxyhexene-1 was 60%. The selectivity with regard to the formation of 14-acetoxytetradecadiene-1,9, was about 65%.

The analysis of the reaction mixture by means of combined gas chromatography and mass spectrography showed the presence of the following expected component in the reaction product:

$CH_2=CH-(CH_2)_6-CH=CH_2$ (decadiene-1,9), $$CH_2=CH-(CH_2)_6-CH=CH-(CH_2)_4-O-\underset{\underset{O}{\|}}{C}-CH_3 \text{ (14-acetoxytetradecadiene-1,9),}$$

$CH_2=CH-(CH_2)_6-CH=CH-(CH_2)_6-CH=CH_2,$ $$CH_3=\underset{\underset{O}{\|}}{C}-O-(CH_2)_4-CH=CH-(CH_2)_6-CH=CH-(CH_2)_4-O-\underset{\underset{O}{\|}}{C}-CH_3,$$

$$CH_3=\underset{\underset{O}{\|}}{C}-O-(CH_2)_4-CH=CH-(CH_2)_4-O-\underset{\underset{O}{\|}}{C}-CH_3.$$

EXAMPLE IV: Reaction between cyclooctene and ethylbut-3-enoate having the formula

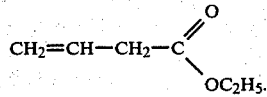

1.69 g (13.94 mM) of ethylbut-3-enoate, 2.4 ml of cyclooctene (18.41 mM) and 24 ml of a suspension which was obtained by mixing 1437 mg of $WCl_6$ with 90 ml of chlorobenzene (this amount corresponds to 0.97 mM of $WCl_6$) were successively introduced into a small round-bottomed 50 ml flask, which was equipped with an inlet for dried nitrogen and an opening which was closed by a self-closing type of rubber stopper and was previously freed from its air- and moisture content by heating under vacuum and subsequent cooling under dry nitrogen. The reaction mixture, which was blue in the beginning, changed to dark red and then to translucent red (homogenous medium). The mixture was heated to a temperature of 50° C. under atmospheric pressure. Then, 0.13 ml (0.96 mM) of $Sn(CH_3)_4$ were added. The color of the reaction medium changed to red, which was becoming darker and darker and then to red-black, and a gas development was observed (the gas undoubtedly was ethylene which was formed by disproportionation of ethylbutenoate with itself). The progress of the reaction was observed by gas chromatography of samples, which were periodically taken from the reaction mixture. In order to stop any further continuation of the reaction in the samples, a small amount of alcohol was added thereto.

After a reaction period of 20 hours at 50° C., the degree of transformation of the cyclooctene was 16.8% and that of the ethylbutenoate was 27.7%. The selectivity with regard to the formation of ethyldodeca-3,11-dienoate was 68%.

The analysis of the reaction mixture by means of combined gas chromatography and mass spectography showed the presence of the following main products:

$CH_2=CH-(CH_2)_6-CH=CH_2,$ $$C_2H_5-\underset{\underset{O}{\|}}{O C}-CH_2-CH=CH-CH_2-\underset{\underset{O}{\|}}{C O}-C_2H_5,$$

$$CH_2=CH-(CH_2)_6-CH=CH-CH_2-\underset{\underset{O}{\|}}{CO\phi}-C_2H_5 \text{ (ethyldodeca-3,11-dienoate).}$$

EXAMPLE V: Reaction between cyclooctene and methylpent-4-enoate having the formula

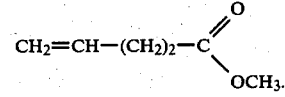

2.34 g of methylpent-4-enoate (20.5 mM), 2.4 ml of cyclooctene (18.41 mM), and 24 ml of a suspension which was obtained by mixing 963 mg of $WCl_6$ with 60 ml of chlorobenzene (this amount corresponded to 0.97 mM of $WCl_6$) were successively introduced into a small 50 ml reactor which was equipped with an inlet for nitrogen and an opening which was closed by a self-closing type of rubber stopper, and which was previously freed from its air- and moisture content by heating under vaccuum and subsequent cooling under dry nitrogen. The reaction mixture, which was blue in the beginning, changed to dark red and then to translucent red (homogenous medium). The mixture was then heated to a temperature of about 50° C. Then 0.13 ml of $Sn(CH_3)_4$ (0.96 mM) were added. The color of the reaction mixture then changed to a darker red (blood-like) color then to black, and a gas development was observed (the gas undoubtedly was ethylene, which was formed by disproportionation of methylpent-4-enoate with itself). The process of the reaction was observed by gas chromatography of samples, which were periodically taken from the reaction mixture. In order to stop any further continuation of the reaction in the samples, a small amount of alcohol was added thereto.

After a reaction period of 20 hours at 50° C., the degree of transformation of the cyclooctene was 35% and that of methylpent-4-enoate was 10%.

The selectivity with regard to the formation of methyltridecad-4,12-ienoate was 32%.

The analysis of the reaction mixture by means of combined gas chromatography and mass spectrography showed the presence of the following main components in the reaction product:

$CH_2=CH-(CH_2)_6-CH=CH_2$,
$CH-(CH_2)_2-COO-CH_3$
$\|$
$CH-(CH_2)_2-COO-CH_3$, and
$CH_2=CH-(CH_2)_6-CH=CH-(CH_2)_2-COO-CH_3$
(methyltrideca-4,12-dienoate).

EXAMPLE VI: Reaction between cyclooctene and ethylpent-4-enoate having the formula

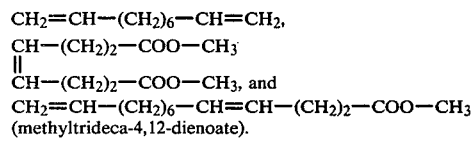

A reaction between the cyclooctene and the ethylpent-4-enoate was carried out under the same reaction conditions which are described in Examples IV and V. The following amount of starting materials were used:
 10.1 mM of ethylpent-4-enoate,
 15.3 mM of cyclooctene,
 24 ml of a solution of $WCl_6$, which was prepared by dissolving 1418 mg of $WCl_6$ in 87 ml of chlorobenzene,
 0.99 mM of $Sn(CH_3)_4$.

After a reaction period of 20 hours at 50° C. under atmospheric pressure, the degree of transformation of the cyclooctene was 53%, and that of ethylpent-4-enoate was 81%.

The selectivity with regard to the formation of ethyltrideca-4,12-dienoate was 36%.

The analysis of the reaction mixture by means of combined gas chromatography and mass spectrography showed the presence of the following main components in the reaction product:

$CH_2=CH-(CH_2)_6-CH=CH_2$,
$CH-(CH_2)_2-COO-C_2H_5$
$\|$
$CH-(CH_2)_2-COO-C_2H_5$, and
$CH_2=CH-(CH_2)_6-CH=CH-(CH_2)_2-COO-C_2H_5$
(ethyltrideca-4,12-dienoate).

The reaction products, which are obtained in the foregoing examples, can be separated into their components by suitable conventional methods which are well known in the art, in particular, by distillation.

EXAMPLE VII: Reaction between cyclooctene and methylhex-5-enoate having the formula

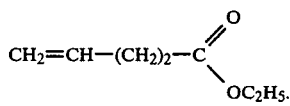

The reaction was carried out according to the procedure described in Examples IV and V. The following amounts of starting materials were used:
 21.0 mM of methylhex-5-enoate,
 18.4 mM of cyclooctene,
 25 ml of a solution of $WCl_6$ which was prepared by dissolving 964 mg of $WCl_6$ in 60 ml of chlorobenzene,
 0.96 mM of $Sn(CH_3)_4$.

After a reaction period of 20 hours at 50° C. under atmospheric pressure, the degree of transformation of the methylhex-5-enoate was 17% and that of cyclooctene was 17%.

The selectivity with regard to the formation of methyltetradeca-5,13-dioenate was 44%.

The analysis of the reaction mixture by means of combined gas chromatography and mass spectography showed the presence of the following main components:

$CH_2=CH-(CH_2)_6-CH=CH_2$,
$CH-(CH_2)_3-COO-CH_3$
$\|$
$CH-(CH_2)_3-COO-CH_3$, and
$CH_2=CH-(CH_2)_6-CH=CH-(CH_2)_3-COO-CH_3$
(methyltetradeca-5,13-dienoate).

EXAMPLE VIII: Reaction between cyclooctene and ethyl 3-hexene-1,6-dioate of the formula $C_2H_5OCO-CH_2-CH=CH-CH_2COOC_2H_5$ 7.10 g (35.5 mM) of ethyl-3-hexene-1,6 dioate, 2.88 g (26.1 mM) of cyclooctene ad 7.7 ml of a solution which was obtained by mixing 674 mg of $WCl_6$ in 20 ml of chlorobenzene (this amount corresponded to 0.65 mM of $WCl_6$) were successively introduced into a small, round bottomed 50 ml glass flask, which was equipped with an inlet for dried nitrogen and an opening which was closed by a self-closing type of stopper, and which was previously freed from its air-and moisture content by heating under vacuum and subsequent cooling under dry nitrogen.

The reaction mixture which was blue in the beginning, changed to a dark red color then to light red and translucent (homogeneous medium). The mixture is stirred for half an hour at room temperature then heated to 20° C. and stirred for half an hour under atmospheric pressure. Then 0.18 ml (1.33 mM) of Sn $(CH_3)_4$ were added. The color of the reaction medium changed to red, which was becoming darker and darker, then to red-black, and a gas development was observed (probably methane). The reaction mixture is heated to 100° C. The progress of the reaction was observed by gas chromatography of samples, which were periodically taken from the reaction mixture. In order to stop any further continuation of the reaction in the samples, a small amount of alcohol was added thereto.

After a reaction period of 48 hours at 100° C. the degree of transformation of the cyclooctene was 41% and that of ethyl-3-hexene-1,6 dioate was 22%. The selectivity with regard to the formation of ethyl 3,11 tetradecadiene-1,14 dioate was about 86%.

The analysis of the reaction mixture by means of combined gas chromatography and mass spectrography showed the presence of the following expected components in the reaction products:

$C_2H_5OCO—CH_2—CH=CH—(CH_2)_6—CH=$
$CH—CH_2—COOC_2H_5$
$C_2H_5—OCO—CH_2—CH=CH—(CH_2)_6—CH=$
$CH—(CH_2)_6—CH=CH—CH_2—COOC_2H_5$

EXAMPLE IX: Reaction between cyclooctene and 1,6-diacetoxy-3-hexene of the formula $CH_3COO—(CH_2)_2—CH=CH—(CH_2)_2—OCOCH_3$ The same procedure as is described in Example VIII was used. The amount of cyclooctene was 3.64 g (33.0 mM). The amount of 1,6-diacetoxy-3-hexene was 6.5 g (32.5 mM). The amount of $WCl_6$ was 0.66 mM and the amount of $Sn(CH_3)_4$ was 1.33 mM.

After a reaction period of 48 hours at 100° C., the degree of transformation of the cyclooctene was 39% and that of 1,6-diacetoxy-3-hexene was 20%.

The selectivity with regard to the formation of 1,14-diacetoxy-3,11-tetradecadiene was about 83%.

The analysis of the reaction mixture by means of combined gas chromatography and mass spectography showed the presence of the following expected components in the reaction product.

$CH_3—COO—(CH_2)_2—CH=CH—(CH_2)_6—CH=$
$CH—(CH_2)_2—O—COCH_3$
$CH_3COO—(CH_2)_2—CH=CH—(CH_2)_6—CH=$
$CH—(CH_2)_6—CH=CH—(CH_2)_2—OCOCH_3$

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for preparing olefins which comprises, successively, the steps of:
   (a) first introducing into a reactor (i) a cyclic olefin of formula I:

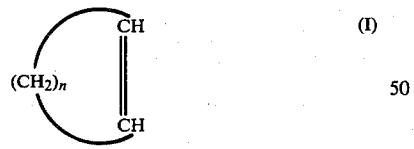

(I)

wherein
      n represents a whole number from 2 to 12, and an acyclic olefin in an amount sufficient to achieve a molar ratio of cyclic to acyclic olefins of from about 0.5 to about 2.0, said acyclic olefin being of formula II:

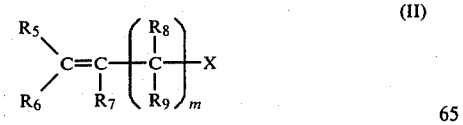

(II)

wherein
      $R_5$ represents hydrogen, methyl, ethyl or the group:

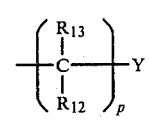

wherein
      $R_{12}$ and $R_{13}$ are the same or different from each other and each represents hydrogen or alkyl containing 1 to 5 carbon atoms;
      Y represents halogen; an acyloxy group $R_{14}—CO—O—$ wherein $R_{14}$ represents alkyl containing 1 to 12 carbon atoms, phenyl or phenylalkyl containing 7 to 12 carbon atoms, or an oxycarbonyl group $R_{15}—O—CO—$, wherein $R_{15}$ represents alkyl containing 1 to 12 carbon atoms, phenyl or phenylalkyl containing 7 to 12 carbon atoms;
      p represents a whole number from 1 to 12 except when Y is an acyloxy group $R_{14}—CO—O—$ wherein P is from 2 to 12;
      $R_6$ and $R_7$ are the same or different from each other and each represents hydrogen methyl or ethyl;
      $R_8$ and $R_9$ are the same or different from each other and each represents hydrogen or alkyl containing 1 to 5 carbon atoms;
      X represents halogen; an acyloxy group $R_{10}—CO—O—$ wherein $R_{10}$ represents alkyl containing 1 to 12 carbon atoms, phenyl or phenyl alkyl, containing 7 to 12 carbon atoms; or an oxycarbonyl group $R_{11}—O—CO$, wherein $R_{11}$ represents alkyl containing 1 to 12 carbon atoms, phenyl or phenyl alkyl, containing 7 to 12 carbon atoms;
      m represents a whole number from 1 to 12 except when X is an acyloxy group $R_{10}—CO—O$ wherein m is from 2 to 12, and optionally (ii) a suitable solvent;
   (b) then introducing into the reactor (i) a solution or suspension of a tungsten oxide salt wherein all or part of the oxygen atoms are replaced by halogen when the solvent is omitted from step (a), and (ii) said tungsten oxide salt being optionally in solid form when a solvent is present in step (a);
   (c) after the reaction mixture from step (b) has become a homogeneous solution, adding thereto an organic-tin compound reducing agent and reacting said cyclic and acyclic olefins at a suitable temperature between about −20 and about 300° C.; and
   (d) recovering a compound of formula III:

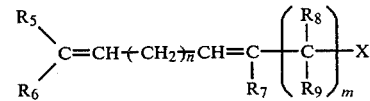

wherein $R_5$, $R_6$, $R_7$, $R_8$, $R_9$, n, m, and X are as defined above.

2. A process for preparing olefins which comprises, successively, the steps of:
   (a) first introducing into a reactor (i) a cyclic olefin from the group consisting of cyclobutene, cyclopentene, cycloheptene, cyclooctene, cyclodecene, and cyclododecene; and an acyclic olefin in an amount sufficient to achieve a molar ratio of cyclic to acyclic olefin of from about 0.5 to about 2.0, said acyclic olefin being selected from the group consisting of methylbutene-3-oate, ethylbutene-3-oate, methylpentene-4-oate, ethylpentene-4-oate, methylpentene-3-oate, ethylpentene-3-oate, methylhexene-5-oate, ethylhexene-5-oate, 4-acetoxybutene-1,5-acetoxypentene-1, 6-acetoxyhexene-1, 4-benzoyloxybutene-1, benzylbutene-3-oate, benzylpentene-3-oate, methyl-3,3-dimethylpentene-4-oate, 4-chlorobutene-1, 5-chloropentene-1, 6-chlorohexene-1, 4-bromobutene-1, 6-bromohexene-1, methyl or ethyl-hexen-3-dioate-1,6; methyl or ethyl-octen-4-dioate-1,8; methyl or ethyl-octen-3-dioate-1,8; methyl or ethyl-decen-5-dioate-1,10; 1,6-diacetoxy-3-hexene; 1,8-diacetoxy-3 or 4 octene; and 1,10-diacetoxy-3 or 4 or 5 decene and optionally (ii) a suitable solvent;

(b) then introducing into the reactor (i) a solution or suspension of a tungsten oxide salt wherein all or part of the oxygen atoms are replaced by halogen selected from the group consisting of $WCl_6$, $WOCl_4WBr_6$, $WOBr_4$, and $WF_6$ when a solvent is omitted from step (a) and (ii) said tungsten oxide salt being optionally in solid form when a solvent is employed in step (a);

(c) after the reaction mixture from step (b) has become a homogeneous solution, adding thereto an organic tin compound reducing agent of the formula $Sn(R)_4$ wherein R represents alkyl and reacting said cyclic and acyclic olefins at a suitable temperature between about $-20°$ and about $300°$ C.; and (d) recovering the metathesis reaction product of said cyclic and acyclic olefins.

3. The process as defined in claim 1, wherein the substituent $R_{10}$ in the formula II represents lower alkyl.

4. The process as defined in claim 1, wherein the substituent $R_{11}$ in the formula II represents lower alkyl.

5. The process as defined in claim 1, wherein the halogen-tungsten salt is selected from the group consisting of $WCl_6$, $WOCl_4$, $WBr_6$, $WOBr_4$, and $WF_6$.

6. The process as defined in claim 5, wherein the halogen-tungsten salt is $WCl_6$.

7. The process as defined in claim 1, wherein the organic tin compound is a compound of the formula $Sn(R)_4$ wherein R represents alkyl.

8. The process as defined in claim 7, wherein the organic tin compounds is $Sn(CH_3)_4$.

9. The process as defined in claim 8, wherein the catalytic composition is consisting essentially of $WCl_6$ and $Sn(CH_3)_4$.

10. The process as defined in claim 1, wherein the molar ratio between the organic tin compound and the halogen-tungsten salt in the catalytic composition is from about 0.5 to about 4.

11. The process as defined in claim 10, wherein the molar ratio is from about 1 to about 2.

12. The process as defined in claim 1, wherein X is alkylcarbonyloxy or alkoxycarbonyl.

13. The process as defined in claim 1 wherein Y is alkylcarbonyloxy or alkoxycarboxy.

14. The process as defined in claim 13, which further comprises the steps of hydrogenating the ester compound of formula III into the corresponding saturated alcohol.

15. The process as defined in claim 13 which further comprises the step of hydrogenating the diester compound of formula III into the corresponding saturated diester.

16. The process as defined in claim 1, wherein the cyclic olefin of formula I is selected from the group consisting of cyclopentene, cyclooctene, cyclodecene, and cyclododecene.

17. The process as defined in claim 2, wherein the acyclic olefin compound of formula II is selected from the group consisting of methylbut-3-enoate, ethylpent-3-enoate, 4-acetoxybut-1-ene and 6-acetoxyhex-1-ene.

18. The process as defined in claim 2, wherein the acyclic olefin compound of formula II is selected from the group consisting of methyl or ethyl-3-hexen-1,6-dioate or 1,6-diacetoxy-3-hexene.

19. The process as defined in claim 7, wherein the solvent is a halogenated aromatic compound.

20. The process as defined in claim 19, wherein the solvent is chlorobenzene.

21. The process as defined in claim 1, wherein the reaction is performed at a temperature of between about 50 and about $150°$ C.

22. The process as defined in claim 1, wherein the reaction is effected under atmospheric pressure.

* * * * *